(12) United States Patent
Lu et al.

(10) Patent No.: US 7,893,805 B2
(45) Date of Patent: Feb. 22, 2011

(54) TRANSFORMER

(75) Inventors: Chih-Ping Lu, Zhubei (TW);
Chih-Shen Chiang, Zhubei (TW)

(73) Assignee: Logah Technology Corp, HsinChu (TW)

( * ) Notice: Subject to any disclaimer, the term of this patent is extended or adjusted under 35 U.S.C. 154(b) by 0 days.

(21) Appl. No.: 12/616,592

(22) Filed: Nov. 11, 2009

(65) Prior Publication Data

US 2010/0123538 A1    May 20, 2010

(30) Foreign Application Priority Data

Nov. 20, 2008  (TW) .............................. 97220748 U

(51) Int. Cl.
*H01F 27/30* (2006.01)
(52) U.S. Cl. ..................................... 336/198
(58) Field of Classification Search ................ 336/65, 336/83, 192, 196, 198, 200, 206–208
See application file for complete search history.

(56) References Cited

U.S. PATENT DOCUMENTS

| | | | |
|---|---|---|---|
| 4,904,974 A * | 2/1990 | Tsuji ........................... | 336/192 |
| 6,369,682 B1 * | 4/2002 | Thompson et al. .......... | 336/192 |
| 6,480,085 B2 * | 11/2002 | Chiang et al. ............... | 336/198 |
| 7,167,069 B2 * | 1/2007 | Haga .......................... | 336/198 |

* cited by examiner

*Primary Examiner*—Tuyen Nguyen
(74) *Attorney, Agent, or Firm*—Chun-Ming Shih

(57) ABSTRACT

A transformer includes a main body and a secondary winding. The main body has a primary winding partition, several secondary winding partitions and two end portions. Several leads are disposed in either end portion. A wire-guiding area is formed in a sunken area in the primary winding partition and a buffer region is formed between the primary end portion and the primary winding partition. The secondary winding is wound around the core on the secondary winding partitions. One end of the wire runs from the secondary winding partitions to the wire-guiding area. Before the secondary wire goes into the buffer region, the secondary wire is folded for several times and then is twisted and rolled for several turns to make the secondary wire thicker. Then the secondary wire goes into the buffer region and then is connected to one of the primary leads. Due to the wire-guiding area and buffer region, the secondary wire would not be affected or pressed against by the primary wire.

3 Claims, 4 Drawing Sheets

TRANSFORMER

BACKGROUND OF THE INVENTION

1. Field of the Invention

The invention generally relates to an improved transformer. More particularly, the invention relates to an improved transformer, in which a buffer region is used to hold the division point formed by the secondary wire so that the secondary wire would not be affected or pressed against by the primary wire and hence would not be prone to breakage. Therefore, quality and reliability of the transformer may be improved.

2. Description of the Prior Art

The coil type transformer has been around for more than 100 years. Many improvements and modifications have been made to improve the coil type transformer. Despite these improvements and modifications, the coil type transformer operates according to the same physical principle, mutual induction.

In the coil type transformer, mutual induction occurs if an emf is induced in a coil because of current changes in a second coil. A primary coil and the secondary coil are wound around the same iron core. The primary coil is connected to the source of electrical energy and the secondary coil is connected to a load. When ac is applied to the primary coil, changes in magnetic flux would occur in the iron core and the changes would cause an ac with the same frequency in the secondary coil. The ratio of primary voltage (or emf) to secondary voltage (or emf) is in proportional to the ratio of the number of turns on the primary coil to the number of turns on the secondary coil. Therefore, if the number of turns on the secondary coil is more than the number of turns on the primary coil, the output voltage is greater than the input voltage and it is called a step-up transformer; conversely, if the number of turns on the secondary coil is less than the number of turns on the primary coil, the output voltage is less than the input voltage and it is called a step-down transformer.

Therefore, coils are the most important parts of the coil type transformer. In addition to the quality of the wires, how winding is done is quiet important. Especially, in small-size step-down transformer, a very fine wire is usually used for the winding; therefore, the wire is prone to breakages (which may lead to a short circuit) and damages if the winding is not done meticulously.

Please refer to FIG. 5, which is a side view illustrating the secondary winding in the transformer of the prior art. The transformer has a main body, a primary winding partition 31 and several secondary winding partitions 32. A secondary wire 42 is wound around the core on the secondary winding partitions 32. One end of the secondary wire passes the primary winding partition 31 and is connected to one of several primary leads 312. Also, the primary wire 41 is wound around the iron core on the primary winding partition 31.

The coil type transformer of the prior art has the following disadvantages:

1. The secondary wire 42 is usually a thinner wire and has to pass the primary winding partition 31. Then the primary wire 41 is wound around the core on the primary winding partition 31. Therefore, the secondary wire 42 is pressed and squeezed by the primary wire 41 and hence is prone to breakage and damage.

2. Before the secondary wire 42 goes into the buffer region, the secondary wire 42 is folded for several times and then is twisted and rolled for several turns to make the wire thicker. Therefore, a division point 421 is formed and is prone to breakage because it is pressed against and squeezed by the primary wire 41.

As a result, the primary winding 41 has to be done meticulously to avoid the breakage of the secondary wire 42. Thus, efficiency in assembly is impeded. In addition, because the division point 421 is buried under the primary wire 41, troubleshooting can not be carried out easily.

In addition, the thicker secondary wire 42 may be easily in twine with or tangled up with the other segment of the secondary wire 42 in the secondary winding partitions 32. This may cause a short circuit of the secondary wire 42. Such short circuit may cause the transformer to burn.

From the above, we can see that the transformer of the prior art has many disadvantages and drawbacks and needs to be improved. To eliminate the disadvantages of the transformer of the prior art, the inventor has put a lot of effort into the subject and has successfully come up with the improved transformer of the present invention.

SUMMARY OF THE INVENTION

An object of the present invention is to provide an improved transformer that has a buffer region so that the division point formed by the secondary wire may be held in the buffer region and that the secondary wire would not be prone to breakage. Therefore, quality and reliability may be improved.

Another object of the present invention is to provide an improved transformer in which the division point is held in the buffer region so that the secondary wire is not prone to breakage. Moreover, thanks to the buffer region, troubleshooting and repair may be done easily and quickly.

A third object of the present invention is to provide an improved transformer in which the secondary wire would not be affected or pressed against by the primary wire and hence would not be prone to breakage. Therefore, stability is improved.

A fourth object of the present invention is to provide an improved transformer in which the thicker secondary wire would not be in twine with or tangled up with the other segment of the secondary wire in the secondary winding partitions so that the short circuit of the secondary wire may be avoided.

To reach these objects, the improved transformer of the present invention is disclosed. The improved transformer of the present invention comprises a main body and a secondary winding. The main body has a primary winding partition, several secondary winding partitions and two end portions. Several leads are disposed in either end portion. A wire-guiding area is formed in a sunken area in the primary winding partition and a buffer region is formed between the primary end portion and the primary winding partition. The primary winding and secondary winding are wound around the iron core on the main body. One end of the secondary wire runs from the secondary winding partitions to the wire-guiding area. Before the secondary wire goes into the buffer region, the secondary wire is folded for several times and then is twisted and rolled for several turns to make the secondary wire thicker. Then the secondary wire goes into the buffer region and then is connected to one of the primary leads. After the winding of the secondary wire is completed, the winding of the primary wire may be started to wind the primary wire around the iron core in the primary winding partition. With the wire-guiding area, the secondary wire would not be affected or pressed against by the primary wire and hence would not be prone to breakage. With the buffer region, the division point is held in the buffer region and hence would not be prone to breakage.

DETAILED DESCRIPTION OF THE PREFERRED EMBODIMENT

Figure 1:
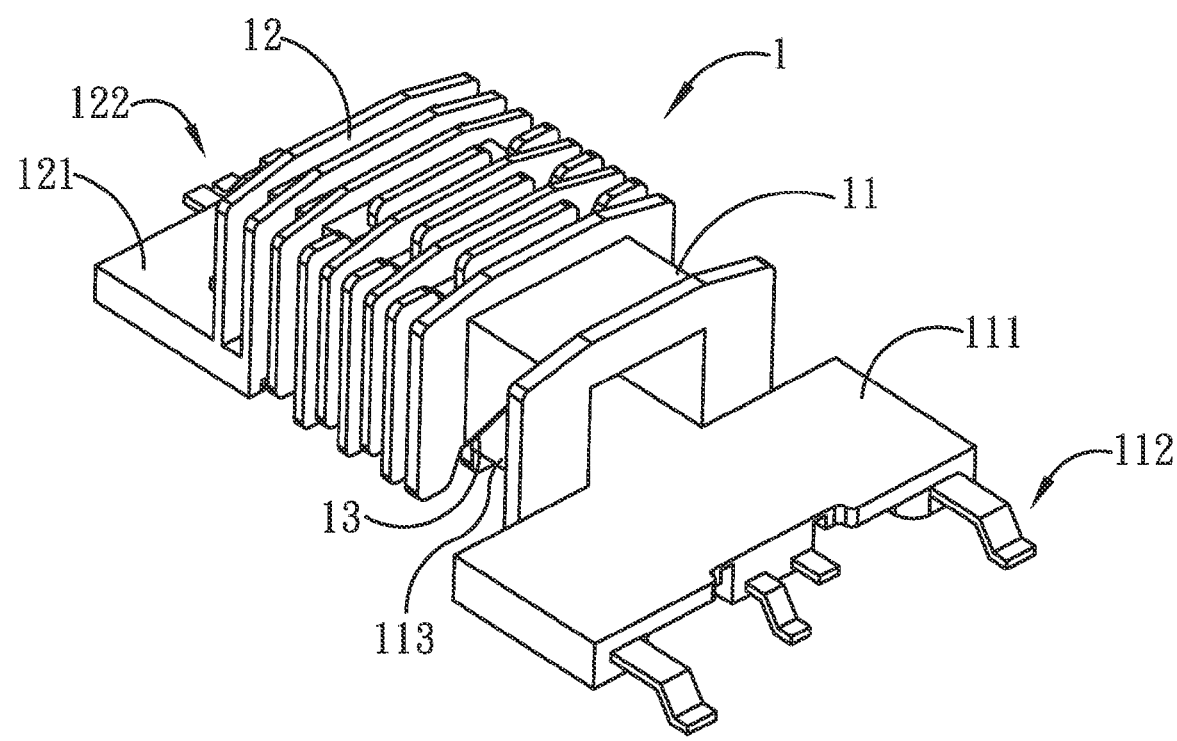
FIG. 1 is a perspective view illustrating the main body of the improved transformer of the present invention.
Figure 2:
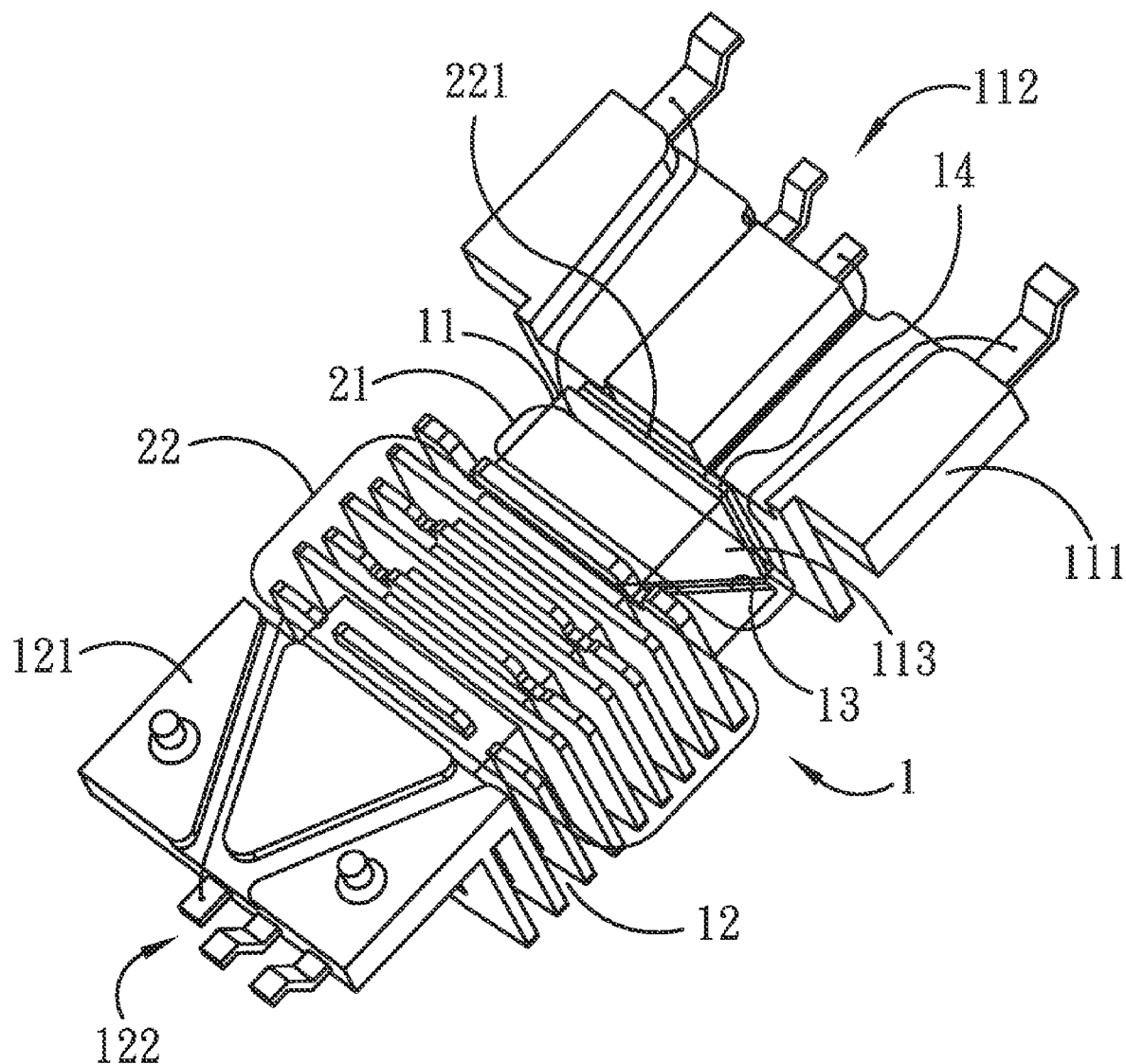
FIG. 2 is a bottom view illustrating the secondary winding in the improved transformer of the present invention.
Figure 3:
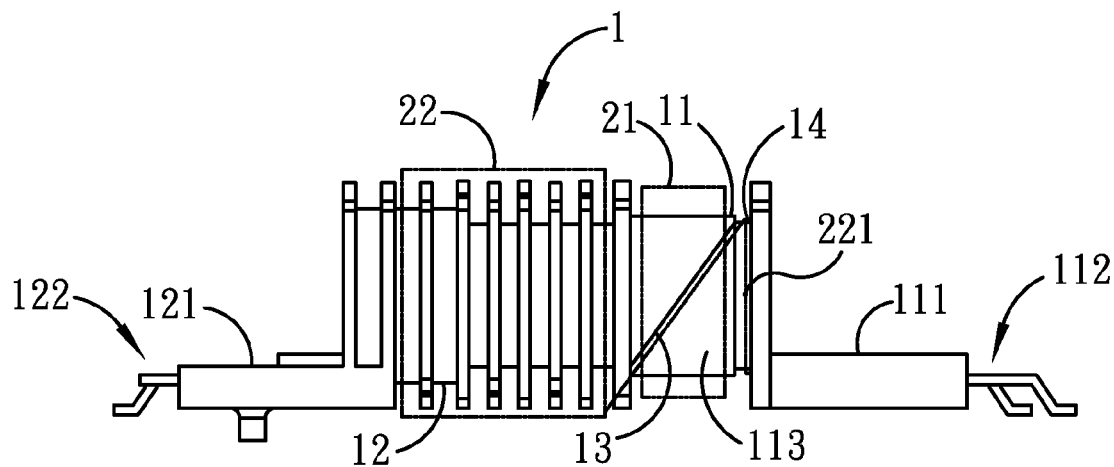
FIG. 3 is a side view illustrating the secondary winding in the improved transformer of the present invention.
Figure 5:
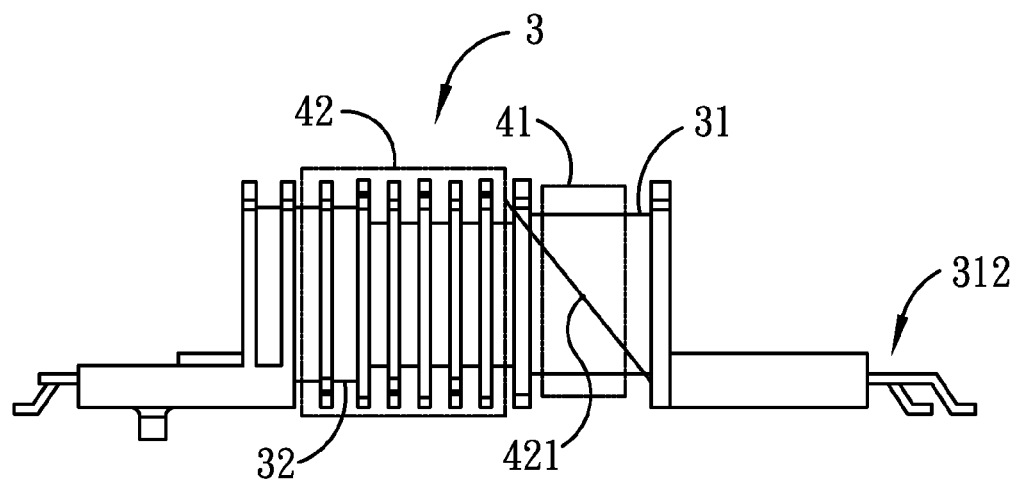
FIG. 5 is a side view illustrating the secondary winding in the transformer of the prior art.

Please refer to FIGS. 1 to 3, which illustrate the improved transformer of the present invention. The improved transformer of the present invention comprises a main body 1 and a secondary winding 22. The main body 1 has a primary winding partition 11 and several secondary winding partitions 12. A primary end piece 111 is disposed near the primary winding partition 11, and several primary leads 112 are provided in the proximal edge of the primary end piece 111. Similarly, a secondary end piece 121 is disposed near the secondary winding partitions 12, and several secondary leads 122 are provided in the distal edge of the secondary end piece 121.

A step-like sunken area 113 is formed on the primary winding partition 11. A wire-guiding area 13 is formed between in the sunken area 113. A buffer region 14 is formed between the primary end piece 111 and the primary winding partition 11. The buffer region 14 is formed in a sunken region between the primary end portion 111 and the proximal primary winding partition 11.

A primary winding 21 and a secondary winding 22 are wound around the iron core on the main body 1. One end of the secondary wire 22 starts from one of the secondary leads 122 and then is wound around the core in the secondary winding partitions 12; the other end of the secondary wire 22 runs from the secondary winding partitions 12 to the wire-guiding area 13. Before the secondary wire 22 goes into the buffer region 14, the wire 22 is folded for several times and then is twisted and rolled for several turns to make the wire 22 thicker. Then the secondary wire 22 goes into the buffer region 14 and then is connected to one of the primary leads 112. With regard to the primary winding 21, the primary wire 21 starts from one of the primary leads 112 and then is wound the core in the primary winding partition 11; next, the primary wire 21 is connected to one of the primary leads 112.

Figure 4:
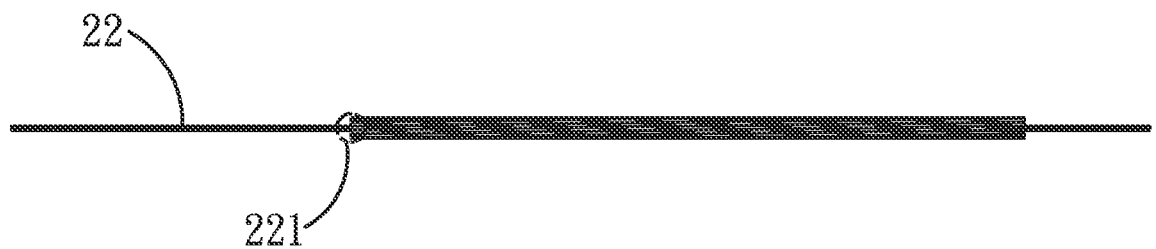
FIG. 4 is a view illustrating the thicker wire formed by the secondary wire.

Now, please refer to FIG. 4. Before the secondary wire 22 goes into the buffer region 14, the wire 22 is folded for several times and then is twisted and rolled for several turns to make the wire 22 stronger and thicker. The key point is that the division point 221, which divides the wire 22 from the thicker wire, is held in the buffer region 14; therefore, the quality of the transformer is enhanced.

In addition, the other end of the secondary wire 22 runs from the secondary winding partitions 12 to the wire-guiding area 13. Because the wire-guiding area 13 is a sunken area in the primary winding partition 11, the secondary wire 22 would not be affected or pressed against by the primary wire 21 and hence would not be prone to breakage. Moreover, the division point 221 is held in the buffer region 14; therefore, the segment around the division point 221 is not prone to breakage in the production. Even if there is a breakage, the breaking point is easily located.

In comparison to the transformer of the prior art, the improved transformer of the present invention has the following advantages:

1. The improved transformer of the present invention has a higher quality and a longer service life because the secondary wire is not prone to breakage caused by the squeezing of the primary wire.

2. In the improved transformer of the present invention, the secondary winding is done in several segments; therefore, troubleshooting and repair may be done easily and quickly.

Although a preferred embodiment of the present invention has been described in detail hereinabove, it should be understood that the preferred embodiment is to be regarded in an illustrative manner rather than a restrictive manner, and all variations and modifications of the basic inventive concepts herein taught still fall within the scope of the present invention.

What is claimed is:

1. A transformer, comprising:
   a main body, having a primary winding partition, several secondary winding partitions and two end portions, wherein several leads are disposed in either end portion, a wire-guiding area is formed in a sunken area in the primary winding partition and a buffer region is formed between the primary end portion and the primary winding partition; and
   a secondary winding, wherein one end of the secondary wire runs from the secondary winding partitions to the wire-guiding area and, before the secondary wire goes into the buffer region, the secondary wire is folded for several times and then is twisted and rolled for several turns to make the secondary wire thicker, and then the secondary wire goes into the buffer region and then is connected to one of the primary leads, due to the wire-guiding area and buffer region, the secondary wire is not pressed and squeezed by the primary wire.

2. The transformer as in claim 1, wherein the buffer region is formed in a sunken region between the primary end portion and the primary winding partition.

3. The transformer as in claim 1, wherein the wire-guiding area is formed in a step-like sunken area in the primary winding partition.

* * * * *